US005342321A

United States Patent [19]

Potter

[11] Patent Number: 5,342,321

[45] Date of Patent: Aug. 30, 1994

[54] LOW PROFILE GASTROSTOMY CATHETER

[75] Inventor: Laurence A. Potter, Flemington, N.J.

[73] Assignee: Teleflex, Inc., Plymouth Meeting, Pa.

[21] Appl. No.: 63,509

[22] Filed: May 18, 1993

[51] Int. Cl.[5] .............................................. A61M 25/04

[52] U.S. Cl. ...................................... 604/174; 604/96; 604/337

[58] Field of Search ................ 604/332, 337, 96, 174, 604/175

[56] References Cited

U.S. PATENT DOCUMENTS

| | | | |
|---|---|---|---|
| 3,802,418 | 4/1974 | Clayton . | |
| 3,893,446 | 7/1975 | Miller . | |
| 3,915,171 | 10/1975 | Shermeta . | |
| 4,393,873 | 7/1983 | Nawash et al. . | |
| 4,579,120 | 4/1986 | MacGregor . | |
| 4,649,913 | 3/1987 | Watson . | |
| 4,685,901 | 8/1987 | Parks . | |
| 4,850,953 | 7/1989 | Haber et al. . | |
| 4,861,334 | 8/1989 | Nawaz . | |
| 5,071,405 | 12/1991 | Piontek et al. | 604/96 |
| 5,167,627 | 12/1992 | Clegg et al. | 604/174 |

FOREIGN PATENT DOCUMENTS

| | | |
|---|---|---|
| 676943 | 2/1930 | France . |
| 1006845 | 4/1952 | France . |
| 2147811 | 5/1985 | United Kingdom . |

OTHER PUBLICATIONS

ENtech, Inc. advertisement entitled Triple–Port Gastrostomy Catheters.

Medical Innovations Corporation advertisement entitled MIC–"KEY" Skin Level Gastrostomy Feeding Kit.

Flexiflo advertisement entitled Obturator, Low Profile Gastrostomy Device, Y–Port Connector With Right Angle Adapter.

Flexiflo advertisement entitled Replacement Gastrostomy Devices.

Sandoz advertisement entitled Gastro–Port.

Bard advertisement entitled The Button Replacement Gastrostomy Device.

Biosearch Medical Products, Inc. Pee Wee A Low Profile Gastrostomy Feeding Kit.

The Gastrostomy Button: A Prospective Assessment of Safety, Success, and Spectrm of Use; 1989; Foutch, et al.

The Gastrostomy "Button"–A Simple, Skin–Level, Nonfluxing Device for Long–Term Enteral Feedings; 1984; Gauderer, et al.

The Gastrostomy Feeding Button; 1987; Hutt, et al.

Feeding Gastrostomy Button: Experience and Recommendations; 1988; Gauderer, et al.

The Gastro–port: An Alternative to the Button; 1991; Faller.

Alternatives in Gastrostomy Management: The Button, 1989; Reynolds, et al.

*Primary Examiner*—Paul J. Hirsch

*Attorney, Agent, or Firm*—Lerner, David, Littenberg, Krumholz & Mentlik

[57] ABSTRACT

A gastrostomy catheter for implantation through a stoma in the abdominal and stomach walls of a patient includes an integral external retention disc designed to be readily engagable by the physician or nursing attendant for manipulation of the feeding tube and inlet ports during use. The inlet ports for feeding nutrients and for fluid passage during balloon inflation are arranged at an inclined angle. This provides easy access to the inlet ports with the required feeding set or inflation syringe without interference with the patient's abdominal wall or the need to manipulate the retention disc in a way which might result in infection of the stoma site.

17 Claims, 2 Drawing Sheets

LOW PROFILE GASTROSTOMY CATHETER

BACKGROUND OF THE INVENTION

The present invention relates in general to the field of surgical appliances, and in particular, to a gastrostomy catheter implantable through a stoma in the abdominal and stomach walls for feeding a patient by delivery of nourishment or other fluids directly into the stomach.

Certain medical conditions require the continuous or repeated percutaneous introduction to bodily organs or tissues of substances such as nutrients, e.g., glucose or drugs. For example, some patients because of injury, malignancy, birth defects or nerve damage may not be able to swallow or otherwise accept nourishment by normal feeding. For this purpose a surgical opening referred to as a stoma is made through the abdominal wall into the stomach. A percutaneous transport tube, referred to herein as a gastrostomy catheter, is inserted through the stoma and used to supply nutrients or other fluids directly into the stomach.

Conventional gastrostomy catheters have a feeding tube which is implanted by surgery through the abdominal wall with the end of the tube terminating directly within the patient's stomach. The gastrostomy catheter is held in place by an inflatable balloon positioned adjacent to the discharge end of the feeding tube. The feeding tube is connected to a movable retention disc which is retained overlying the stoma in the patient's abdominal wall through which the feeding tube has been implanted. Conventional gastrostomy catheters typically include a pair of passageways respectively communicating with the interior of the feeding tube and inflatable balloon.

During use of the gastrostomy catheter, it may be required to reposition the orientation of the feeding tube and/or passageways which has previously been achieved by rotating the retention disc. Owing to the small size and disc-like shape of the retention disc, manipulation could only be achieved by pressing one's fingers into the abdominal wall under the retention disc in order to sufficiently engage the retention disc for rotation. However, this has the potential to lead to the infection of the stoma site as a result of bacteria present on one's fingers. Infection of the stoma site in this manner can also occur during removal of the gastrostomy catheter after patient recovery.

The known design of these retention discs is such to receive connection via respective inlet ports to a feeding tube set for the delivery of nutrients and to a syringe for inflation of the catheter's balloon. The arrangement of these connections has to date been such to cause interference with the feeding tube set during minimal patient activity. In addition, the connection of a syringe to the inflation inlet port has frequently resulted in interference with the patient's abdominal wall requiring manipulation of the retention disc by one's fingers which, once again, has the tendency for potential infection at the stoma site.

Accordingly, there is an unsolved need for a gastrostomy catheter which overcomes the hereinbefore disadvantages resulting from the construction of the known gastrostomy catheters, and which provides advantages during use which have hereinbefore been unknown.

SUMMARY OF THE INVENTION

It is one object of the present invention to provide a low profile gastrostomy catheter which enables manipulation of the feeding tube with minimal possibility of infection at the stoma site.

Another object of the present invention is to provide a low profile gastrostomy catheter which facilitates and provides for more convenient connection of feeding tube sets and syringes for balloon inflation without interference with the patient's abdominal will and/or the need for manipulation for the retention disc.

Another object of the present invention is to provide a low profile gastrostomy catheter which facilitates clinical treatment of a patient in need of direct feeding to one's stomach.

In accordance with one embodiment of the present invention, there is disclosed a gastrostomy catheter for implantation through a stoma in the abdominal and stomach walls of a patient, the catheter comprising a feeding tube for passage of fluids therethrough, inflatable means positioned about the feeding tube for securing the feeding tube within the stomach of a patient when inflated, a body attached to the feeding tube engagable by one's fingers to enable manipulation thereof and to permit removal of the feeding tube from implantation without contacting one's fingers with a portion of the patient's abdominal wall adjacent the stoma, and a pair of passageways within the body in respective communication with the feeding tube for the passage of fluids therethrough and the inflatable means for the passage of a fluid thereinto for inflating the inflatable means, the passageways arranged at an incline to facilitate connection to a fluid supply and a fluid source without interference with the abdominal wall of a patient.

In accordance with another embodiment of the present invention, there is disclosed a gastrostomy catheter for implantation through a stoma in the abdominal and stomach walls of a patient, the catheter comprising a feeding tube having an inlet end and an outlet end for passage of fluids therethrough, inflatable means positioned between the inlet end and the outlet end of the feeding tube for securing the feeding tube within the stomach of a patient when inflated, an inflation tube having an inlet end and an outlet end communicating with the inflatable means for the passage of a fluid therethrough, a body attached to the inlet ends of the feeding tube and the inflation tube, the body engagable by one's fingers to enable manipulation thereof and to permit removal of the feeding tube from implantation without contacting one's fingers with a portion of the patient's abdominal wall adjacent the stoma, a first passageway within the body in communication with the inlet end of the feeding tube for the passage of fluids therethrough, the first passageway having an inlet portion arranged at an incline to facilitate connection to a fluid supply without interference with the abdominal wall of the patient, and a second passageway within the body in communication with the inlet end of the inflation tube for the passage of a fluid therethrough for inflating the inflatable means, the second passageway having an inlet portion arranged at an incline to facilitate connection to a fluid source without interference with the abdominal wall of a patient.

In accordance with another embodiment of the present invention, there is disclosed a gastrostomy catheter for implantation through a stoma in the abdominal and stomach walls of a patient, the catheter comprising a feeding tube having an inlet end and an outlet end for passage of fluids therethrough, an inflatable balloon positioned between the inlet end and the outlet end of the feeding tube for securing the feeding tube within the stomach of a patient when inflated, an inflation tube having an inlet end and an outlet end communicating with the inflatable balloon for the passage of a fluid therethrough, a body having a pair of spaced sidewalls and a pair of spaced endwalls attached to the inlet ends of the feeding tube and the inflation tube, the body including a base surrounding the feeding tube and having a surface positionable overlying the region of the stoma within the patient, the body engagable by one's fingers to enable manipulation thereof and to permit removal of the feeding tube from implantation without contacting one's fingers with a portion of the patient's abdominal wall adjacent the stoma, a first passageway within the body in communication with the inlet end of the feeding tube for the passage of fluids therethrough, the first passageway having an inlet portion extending to one sidewall of the body and arranged at an angle of less than about 45° to the surface of the body to facilitate connection to a fluid supply without interference with the abdominal wall of the patient, and a second passageway within the body in communication with the inlet end of the inflation tube for the passage of a fluid therethrough for inflating the inflatable balloon, the second passageway having an inlet portion extending to the other sidewall of the body and arranged at an angle of less than about 45° to the surface of the body to facilitate connection to a fluid source without interference with the abdominal wall of a patient.

BRIEF DESCRIPTION OF THE DRAWINGS

The above description, as well as further objects, features and advantages of the present invention will be more fully understood with reference to the following detailed description of a low profile gastrostomy catheter, when taken in conjunction with the accompanying drawings, wherein.

DETAILED DESCRIPTION OF THE PREFERRED EMBODIMENT

Figure 1:
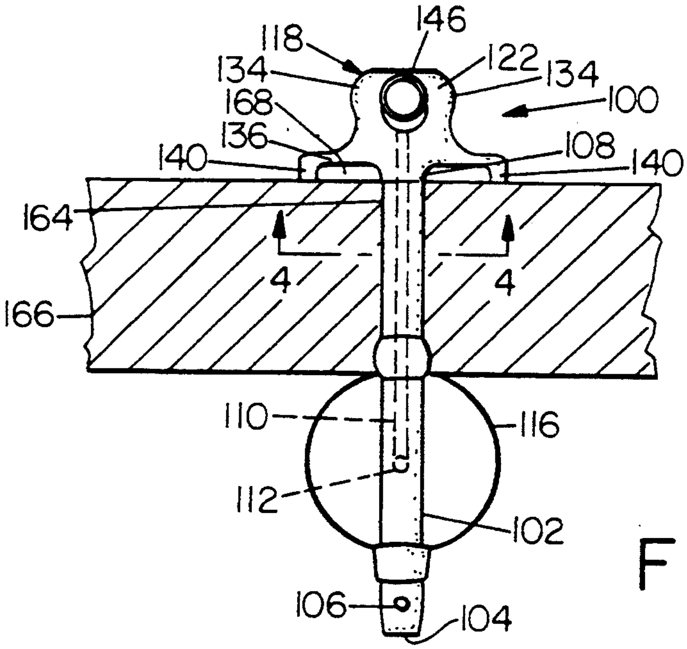
FIG. 1 is a side elevational view, in partial cross-section showing a gastrostomy catheter constructed in accordance with the present invention implanted through a stoma in the abdominal and stomach walls of a patient.

Referring now to the drawings wherein like reference numerals represent like elements, there is shown in FIG. 1 a low profile gastrostomy catheter constructed in accordance with one embodiment of the present invention and generally designated by reference number 100. Referring to the drawings in general, the gastrostomy tube 100 includes a longitudinally extending hollow feeding tube 102 having a longitudinal axis 103 and an open outlet end 104 encircled by one or more openings 106 and an open inlet end 108. Integrally formed with the feeding tube 102 is an internal inflation lumen 110 terminating at an outlet opening 112 and an inlet opening 114 which is adjacent the inlet end 108 of the feeding tube 102. Positioned about the feeding tube 102 adjacent the outlet end 104 and overlying the outlet opening 112 of the inflation lumen 110 is an inflatable balloon 116. As thus far described, it is to be understood that the gastrostomy catheter 100 with respect to the feeding tube 102, inflation lumen 110 and inflatable balloon 116 is of conventional design.

Figure 2:
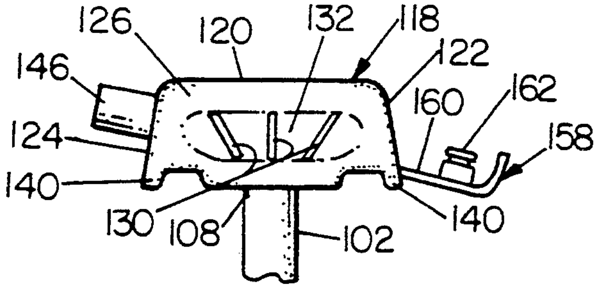
FIG. 2 is a side elevational view of the retention disc of the gastrostomy catheter in accordance with one embodiment of the present invention.
Figure 3:
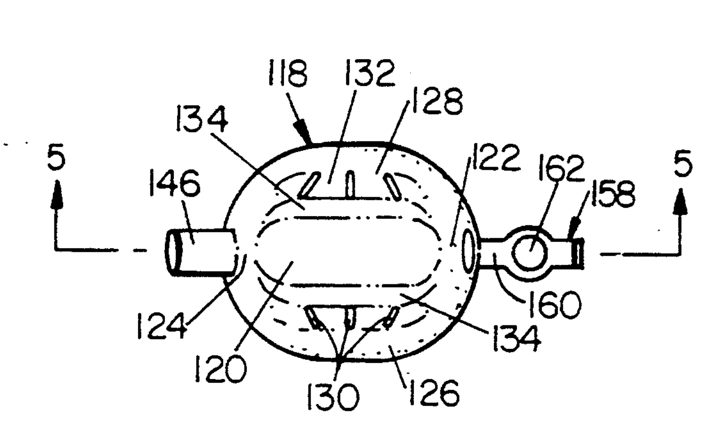
FIG. 3 is a top plan view of the retention disc of the gastrostomy catheter in accordance with one embodiment of the present invention.

Attached to the inlet end 108 of the feeding tube 102 and the inlet opening 114 of the inflation lumen 110 is a retention disc 118. The retention disc 118 includes a body 120 of generally rectangular-like shape having a pair of spaced endwalls 122, 124 and a pair of spaced sidewalls 126, 128. The sidewalls 126, 128 support a plurality of angled protruding ridges 130 within a recess portion 132 formed below bulges 134, as best shown in FIGS. 1 and 2.

Figure 4:
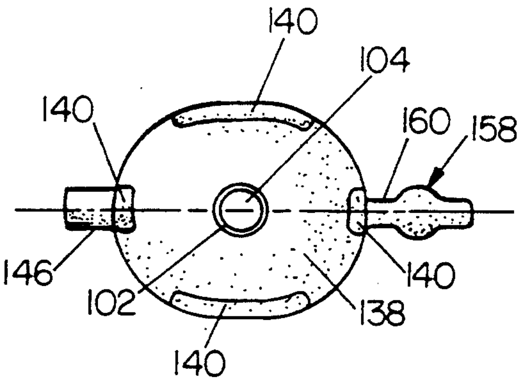
FIG. 4 is a bottom plan view taken along Line 4—4 in FIG. 1 of the retention disc in accordance with one embodiment of the present invention.

The body 120 of the retention disc 118 is integrally formed with an oval shaped base 136 having an underlying surface 138 as best shown in FIG. 4. A plurality of protruding ridges 140 are integrally formed extending upwardly from and circumferentially arranged around the perimeter of the surface 138.

Figure 5:
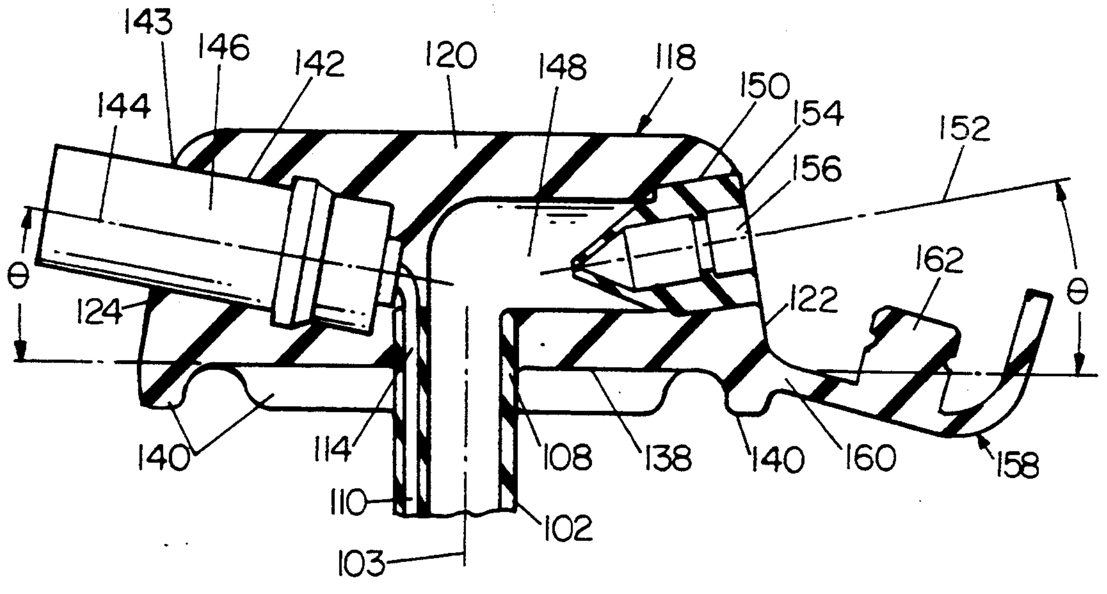
FIG. 5 is a cross-sectional view taken along Line 5—5 in FIG. 3 of the retention disc in accordance with one embodiment of the present invention.

Referring now to FIG. 5, the inlet opening 114 of the inflation lumen 110 is in communication with a passageway 142 extending through the body 120 at an angle to the longitudinal axis 103 of the feeding tube 102 to an inlet opening 143 in endwall 124. The passageway 142 has a longitudinal axis 144 arranged at an incline so as to form an angle with a plane containing surface 138 of the retention disc 118. The angle of inclination is preferably less than 45°, and in accordance with the preferred embodiment 13°. Received within the open passageway 142 in communication with the inflation lumen 110 is a balloon inflation valve 146. The inflation valve 146 is of conventional design to prevent deflating of the balloon 116 by blocking fluid flow, i.e., water or gas, in the reverse direction until released by the insertion of a syringe Luer fitting as is well known in the gastrostomy catheter art.

The inlet end 108 of the feeding tube 102 is connected to a passageway 148 having an inlet portion 150 which extends through the body 120 at an angle to the longitudinal axis 103 of the feeding tube 102 and which terminates at endwall 122. The inlet portion 150 is arranged at an incline having its longitudinal axis 152 arranged at an angle to surface 138 of the retention disc 118. The longitudinal axis 152 of the inlet portion 150 is arranged at an angle preferably of less than 45°, and in accordance with the preferred embodiment 20°. The inlet opening 143 of passageway 142 and the inlet portion 150 of passageway 148 are arranged within the body 120 in co-linear alignment as shown in FIG. 4. An anti-reflux valve 154 of conventional design is received within the inlet portion 150 which prevents reverse flow of fluids through the feeding tube 102. The valve 154 is provided with an inlet opening 156 constructed to accommodate a feeding tube set or other connecting device such as a Luer syringe.

A plug assembly 158 is integrally joined to the retention disc 118 by means of a strap 160 which supports a solid cylinder 162 sized for interference fit within inlet opening 156 of the valve 154. The plug assembly 158 thereby enables closing of the inlet opening 156 during periods of non-use to prevent possible contamination. The components of the gastrostomy catheter 100, as thus far described, may be constructed from a variety of materials, for example, silicone biomaterial which is preferred for patient compatibility and reliability.

Referring to FIG. 1, the gastrostomy catheter 100 is inserted into a patient through a previously prepared stoma 164 created in the abdominal wall 166 using preexisting surgical procedures. The feeding tube 102 with surrounding uninflated balloon 116 is inserted through the stoma 164 into the patient's stomach. The retention disc 118 is situated raised slightly away from the abdominal wall 166 by means of the ridges 140 to form an air passage 168. The air passage 168 permits the entry of air between the skin and the retaining disc 118 to reduce the likelihood of adverse skin effects that might otherwise possibly occur if the entire retention disc was in direct contact with the patient's skin and stoma 164. In addition, the resultant air exposure to the surgical stoma 164 provides a constant source of oxygen to promote healing and to minimize the possibility of infection.

The gastrostomy catheter 100 is retained after implantation by inflating balloon 116 which forms a gasket that seals the entrance to the stoma 164 within the stomach and, along with the retention disc 118 on the abdomen, secures the catheter in place.

The balloon 116 is inflated by, for example, the use of a syringe which is inserted into the inflation valve 146 so as to inject a fluid through the inflation lumen 110 and into the balloon 116. As previously described, the inflation valve 146 is arranged at an inclined angle which extends upwardly away from the patient's abdominal wall. This inclined angle enables the physician or nursing attendant to properly position the syringe for receipt into the inflation valve 146 without interference with the patient's abdominal wall. In the absence of the foregoing arrangement, and in view of the relatively large size of the typical syringe employed, it would be necessary to depress the syringe body into the patient's abdominal wall or to manipulate the retention disc 118 in order to properly insert the syringe into the inflation valve 146. The foregoing procedure can cause injury to the abdominal wall as well as possible infection of the stoma 164 as a result of potential contact with one's fingers during manipulation of the retention disc as described hereinbefore.

Nutrients or other fluids may be fed to the feeding tube 102 using a conventional feeding set (not shown) which is connectable to the inner opening 156 in the valve 154. The inclined angular arrangement of the inlet opening 156 avoids the same problems as previously addressed with respect to the inflation of the balloon 116 through the inflation valve 146. In this regard, a feeding set or syringe may be readily connected to the valve 154 without interference with the patient's abdominal wall or manipulation of the retention disc 118 which might result in infection of the stoma 164.

The gastrostomy catheter 100 is removed from the patient by first deflating balloon 116 in a reverse procedure to its inflation using a syringe inserted into the inflation valve 146 and aspirating the balloon contents. The retention disc 118 is gripped with one's fingers within the recessed portions 132 within the sidewalls 126, 128. Gripping of the retention disc 118 by one's fingers is enhanced by the presence of the ridges 130 which minimize potential slippage. Due to the relevantly large size of the retention disc 118, it is easily engaged by one's fingers to obtain a secure grasp. The gastrostomy catheter 100 may accordingly be removed by gently pulling outwardly away from the patient's abdomen. This construction of the retention disc 118 facilitates removal of the gastrostomy catheter 100 in a manner which minimizes trauma to the abdominal wall or contact with the stoma 164 with one's fingers as was required by the prior known low profile gastrostomy catheters. In addition, the readily graspable retention disc 118 enables manipulation of the gastrostomy catheter 100 when in place in order to position the inlet opening 156 for receiving a feeding set at the most convenient orientation to minimize interference with its extended tubing.

Although the invention herein has been described with references to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A gastrostomy catheter for implantation through a stoma in the abdominal and stomach walls of a patient, said catheter comprising a feeding tube for passage of fluids therethrough, inflatable means positioned about said feeding tube for securing said feeding tube within the stomach of a patient when inflated, a body attached to said feeding tube engagable by one's fingers to enable manipulation of said feeding tube and to permit removal of said feeding tube from implantation without contacting one'fingers with a portion of the patient's abdominal wall adjacent the stoma, said body including a base surrounding said feeding tube having a surface positionable overlying the region of the stoma within the patient, and a pair of passageways within said body in respective communication with said feeding tube for the passage of fluids therethrough and said inflatable means for the passage of a fluid thereinto for inflating said inflatable means, said passageways each arranged at an inclined angle to said surface of said body to facilitate connection to a fluid supply and a fluid source without interference with the abdominal wall of a patient.

2. The gastrostomy catheter of claim 1, wherein said pair of passageways are arranged in co-linear alignment within said body.

3. The gastrostomy catheter of claim 1, wherein said inflation means comprises a balloon.

4. The gastrostomy catheter of claim 1, wherein said body has a rectangular-like shape, said body having a pair of spaced endwalls having openings in communication with said passageways and a pair of spaced sidewalls.

5. The gastrostomy catheter of claim 4, further including a plurality of ridges supported on said sidewalls to facilitate engagement of said body by one's fingers.

6. The gastrostomy catheter of claim 1, further including a plurality of ridges on said surface to provide an air passageway to the stoma between said surface of said base and the abdominal wall of a patient.

7. The gastrostomy catheter of claim 1, wherein said passageways are arranged at an angle of less than 45° to said surface of said body.

8. The gastrostomy catheter of claim 7, wherein said passageways are arranged at respective angles of 13° and 20°.

9. A gastrostomy catheter for implantation through a stoma in the abdominal and stomach walls of a patient, said catheter comprising a feeding tube an inlet end and an outlet end for passage of fluids therethrough, inflatable means positioned between said inlet end and said outlet end of said feeding tube for securing said feeding tube within the stomach of a patient when inflated, an inflation tube having an inlet end and an outlet end communicating with said inflatable means for the passage of a fluid therethrough, a body attached to the inlet ends of said feeding tube and said inflation tube, said body engagable by one's fingers to enable manipulation thereof and to permit removal of said feeding tube from implantation without contacting one's fingers with a portion of the patient's abdominal wall adjacent the stoma, said body including a base surrounding said feeding tube having a surface positionable overlying the region of the stoma within the patient, a first passageway within said body in communication with said inlet end of said feeding tube for the passage of fluids therethrough, said first passageway having an inlet portion arranged at an inclined angle to said surface of said body to facilitate connection to a fluid supply without interference with the abdominal wall of the patient, and a second passageway within said body in communication with said inlet end of said inflation tube for the passage of a fluid therethrough for inflating said inflatable means, said second passageway having an inlet portion thereof arranged at an inclined angle to said surface of said body to facilitate connection to a fluid source without interference with the abdominal wall of a patient.

10. The gastrostomy catheter of claim 9, wherein said first passageway and said second passageway are arranged in co-linear alignment within said body.

11. The gastrostomy catheter of claim 9, wherein said inflation means comprises a balloon.

12. The gastrostomy catheter of claim 9, wherein said body has a rectangular-like shape, said body having a pair of spaced endwalls containing the inlet portions of said first and second passageways and a pair of spaced sidewalls.

13. The gastrostomy catheter of claim 12, further including a plurality of ridges supported on said sidewalls to facilitate engagement of said body by one's fingers.

14. The gastrostomy catheter of claim 9, further including closure means for said inlet portion of said first passageway.

15. The gastrostomy catheter of claim 11, further including a plurality of ridges on said surface to provide an air passageway to the stoma between said surface of said base and the abdominal wall of a patient.

16. The gastrostomy catheter of claim 11, wherein the inlet portions of said first and second passageways are arranged at an angle of less than 45° to said surface of said body.

17. A gastrostomy catheter for implantation through a stoma in the abdominal and stomach walls of a patient, said catheter comprising a feeding tube having an inlet end and an outlet end for passage of fluids therethrough, an inflatable balloon positioned between said inlet end and said outlet end of said feeding tube for securing said feeding tube within the stomach of a patient when inflated, an inflation tube having an inlet end and an outlet end communicating with said inflatable balloon for the passage of a fluid therethrough, a body having a pair of spaced sidewalls and a pair of spaced endwalls attached to the inlet ends of said feeding tube and said inflation tube, said body including a base surrounding said feeding tube and having a surface positionable overlying the region of the stoma within the patient, said body engagable by one's fingers to enable manipulation thereof and to permit removal of said feeding tube from implantation without contacting one's fingers with a portion of the patient's abdominal wall adjacent the stoma, a first passageway within said body in communication with said inlet end of said feeding tube for the passage of fluids therethrough, said first passageway having an inlet portion extending to one said sidewall of said body and arranged at an angle of less than about 45° to said surface of said body to facilitate connection to a fluid supply without interference with the abdominal wall of the patient, and a second passageway within said body in communication with said inlet end of said inflation tube for the passage of a fluid therethrough for inflating said inflatable balloon, said second passageway having an inlet portion extending to the other said sidewall of said body and arranged at an angle of less than about 45° to said surface of said body to facilitate connection to a fluid source without interference with the abdominal wall of a patient.

* * * * *

UNITED STATES PATENT AND TRADEMARK OFFICE

CERTIFICATE OF CORRECTION

PATENT NO. : 5,342,321

DATED : August 30, 1994

INVENTOR(S) : Laurence A. Potter

It is certified that error appears in the above-identified patent and that said Letters Patent is hereby corrected as shown below:

On the cover page, "Other Publications", second column, "Spectrm" should read --Spectrum--.

Column 2, line 7, "will" should read --wall--.

Column 6, line 31, "one'" should read --one's--.

Signed and Sealed this

Twentieth Day of December, 1994

Attest:

BRUCE LEHMAN

Attesting Officer

*Commissioner of Patents and Trademarks*